United States Patent [19]

Kelton et al.

[11] Patent Number: 5,240,832
[45] Date of Patent: Aug. 31, 1993

[54] HETEROPOLYMERIC PROTEIN PRODUCTION METHODS

[75] Inventors: Christie A. Kelton, Hopkinton; Noreen P. Nugent, Framingham; Scott C. Chappel, Boston, all of Mass.

[73] Assignee: Genzyme Corporation, Cambridge, Mass.

[21] Appl. No.: 780,556

[22] Filed: Oct. 16, 1991

Related U.S. Application Data

[63] Continuation of Ser. No. 368,628, Jun. 20, 1989, abandoned.

[51] Int. Cl.⁵ .................... C12P 21/02; C12N 15/16; C12N 15/85
[52] U.S. Cl. .................. 435/69.4; 435/320.1; 435/172.3; 435/240.2; 435/69.1; 536/23.51; 536/23.5; 536/23.1; 935/6; 935/13; 935/66; 935/70; 935/34; 935/60; 935/61; 930/110
[58] Field of Search .................. 435/91, 172.3, 320.1, 435/317.1, 252.3, 240.2, 69.1, 70.1, 70.2; 935N/9, 10, 13; 536/27, 23, 51; 530/398

[56] References Cited

U.S. PATENT DOCUMENTS 4,840,896  6/1989  Reddy et al. ................. 435/69.4

OTHER PUBLICATIONS

Watanabe et al, 1987. Biochem. Biophys. Res. Commun. 149, 1149–1155.
Matzuk et al. 1987 Proc. Nat'l Acad. Sci. USA. 84, 6354–6358.
Matzuk et al, 1988. J. Cell Biol. 106, 1049–1059.
Matzuk et al. 1988. Molec. Endocrinol. 2, 95–100.
Fiddes et al, 1981. J. Molec. Appl. Genet. 1, 3–18.
Fiddes et al, 1979. Nature 281, 351–355.
Goodwin et al, 1983. Nuc. Acids Res. 11, 6873–6882.
Kaetzel et al. 1986. J. Biol. Chem. 263, 6344–6351.
Kaetzel et al. 1985. Proc. Nat'l Acad. Sci. USA 82, 7280–7283.
Talmadge et al. Nature 307, 37–40.
Beck et al., 685 DNA 4, 76.
Medeiros-Neto et al. (eds.) in: *Frontiers in Thyroidology.* Plenum Medical Book Co., New York, pp. 173–176.
Chin et al. 1983. Proc. Nat'l Acad. Sci. USA. 80, 4649–4653.
Kozak et al. 1984, Nucleic Acids Res. 12, 857–872.
Wondisford et al. 1988 J. Biol. Chem. 263, 12538–12542.
Watkins et al. 1987. DNA 6, 205–212.
Tatsumi et al. Gene 73, 489–497.

*Primary Examiner*—Christopher S. F. Low

[57] ABSTRACT

Cultured mammalian cells transfected with new vectors comprising full-length or partial α and β subunit genomic DNA sequences produce significantly higher levels of dimeric glycoprotein hormone than do cells transfected with α and β subunit cDNA sequences. In cases where only the cDNA clones are available, the cDNA sequences can be used in new expression vectors comprising introns or other important genomic regions from a homologous or heterologous source.

6 Claims, 6 Drawing Sheets

* - DHFR, ODC or tPA

HETEROPOLYMERIC PROTEIN PRODUCTION METHODS

This is a continuation of copending application Ser. No. 07/368,628 files on Jun. 20, 1989, now abandoned.

FIELD OF INVENTION

This invention relates to expression systems for the production of heteropolymeric proteins from transformed mammalian cells and more particularly concerns novel expression systems and vectors for the production of dimeric glycoprotein hormones.

BACKGROUND OF THE INVENTION

Transfection of the $\alpha$ and $\beta$ subunit cDNA clones into cultured mammalian cells has characteristically resulted in low gonadotropin expression levels. This has seriously impeded the production of these hormones on a commercial scale.

It is one aspect of the present invention to provide commercially practical methods for the production of such hormones.

While some genes, such as $\beta$-globin (1, 2) and immunoglobulin genes (3–5), require introns for optimal mRNA production, other genes, such as thymidine kinase (6), do not. Intron-dependent increases in gene expression can result from either non-transcriptional (e.g. globin genes) or transcriptional (e.g. immunoglobulin genes) mechanisms.

Isolation of the genes which encode the human and bovine common $\alpha$, FSH$\beta$, LH$\beta$, and human TSH$\beta$ subunits has been reported (8–14). Ramabhadran et al. (15) first described transfection with and subsequent expression of the human alpha subunit cDNA in mouse cells. Several groups have since reported successful expression of dimeric glycoprotein hormones by transfection of cultured mammalian cells. Some of these groups (16, 17) employed cDNA clones while others (14, 18, 19) have used intron-containing cDNA or genomic sequences.

U.S. Pat. No. 4,840,866 and U.S. Pat. No. 4,923,805 describe the use of cDNA clones (without introns) to produce gonadotropins in cultured mammalian cells. While those expression systems yield biologically active molecules, the yield of the transformed mammalian cells are generally lower than described.

It is another aspect of the present invention to provide improved expression systems, useful with gonadotropins, which result in higher yield.

Matzuk and Boime (18a) mention that an intron inserted into the coding region of the human $\alpha$ subunit cDNA improved expression results compared with the use of cDNA clones but provided no data to support that contention or specific description of their methods. In a recent publication, Kaetzel and Nilson (7) reported relatively high levels of bovine LH expression in CHO cells. Their system employed genomic sequences for expression of both the $\alpha$ and LH$\beta$ subunits. However, the effect of genomic sequences versus cDNA sequences upon LH expression was not addressed in their paper.

It is yet another aspect of the present invention to obviate the confusion represented by the present state of the art and to provide the critical teaching necessary to derive improved vectors encoding dimeric glycoproteins and production methods utilizing such vectors.

Introns have been linked to increased mRNA accumulation in tissue culture cells for rabbit $\beta$-globin (1,2,20), E. coli gpt (20), and mouse DHFR (20, 21). Examples of genes containing introns with enhancer elements which increase transcription are the immunoglobulin genes (3–5), the rat cytochrome c gene (22), and the human pro-$\alpha$1(I) collagen gene (23). Introns have also been shown to result in increased transcriptional efficiency in transgenic mice for the following genes: rat growth hormone, mouse metallothionein-I, and human $\beta$-globin (24). However, introns have no effect on the expression of these last three genes when they are transfected into cultured mammalian cells.

It has been shown that expression levels can be influenced by different 3' untranslated and polyadenylation regions (24, 25). For example, higher expression levels of a galK marker gene result if the bovine growth hormone polyadenylation region is used for transcription termination rather than the SV40 early or human collagen polyadenylation regions (24).

SUMMARY

In accordance with the various principles and aspects of the present invention there are provided novel expression systems employing the use of $\alpha$ subunit genomic sequences, or $\alpha$ subunit cDNA constructions with an added intron, which significantly and surprisingly enhance dimeric glycoprotein hormone production in mammalian cells. This discovery will facilitate the development of processes for high-yield production of dimeric glycoprotein hormones which share the common $\alpha$ subunit. These include chorionic gonadotropin (GG), follicle stimulating hormone (FSH), luteinizing hormone (LH), and thyroid stimulating hormone (TSH).

It has also been unexpectedly discovered that TSH$\beta$ subunit gene expression is intron-dependent. Characterization of the genomic regions necessary for optimal expression of the TSH$\beta$ subunit now made possible by the instant invention provide critical and specific information regarding the development of a process for efficient production of dimeric TSH.

BRIEF DESCRIPTION OF THE DRAWINGS

Further understanding of the various aspects and principles of the present invention may be had by study of the accompanying figures wherein.

DETAILED DESCRIPTION AND BEST MODE

Example 1

Plasmid constructions for the expression of the common α and FSHβ subunits

Figure 1A:
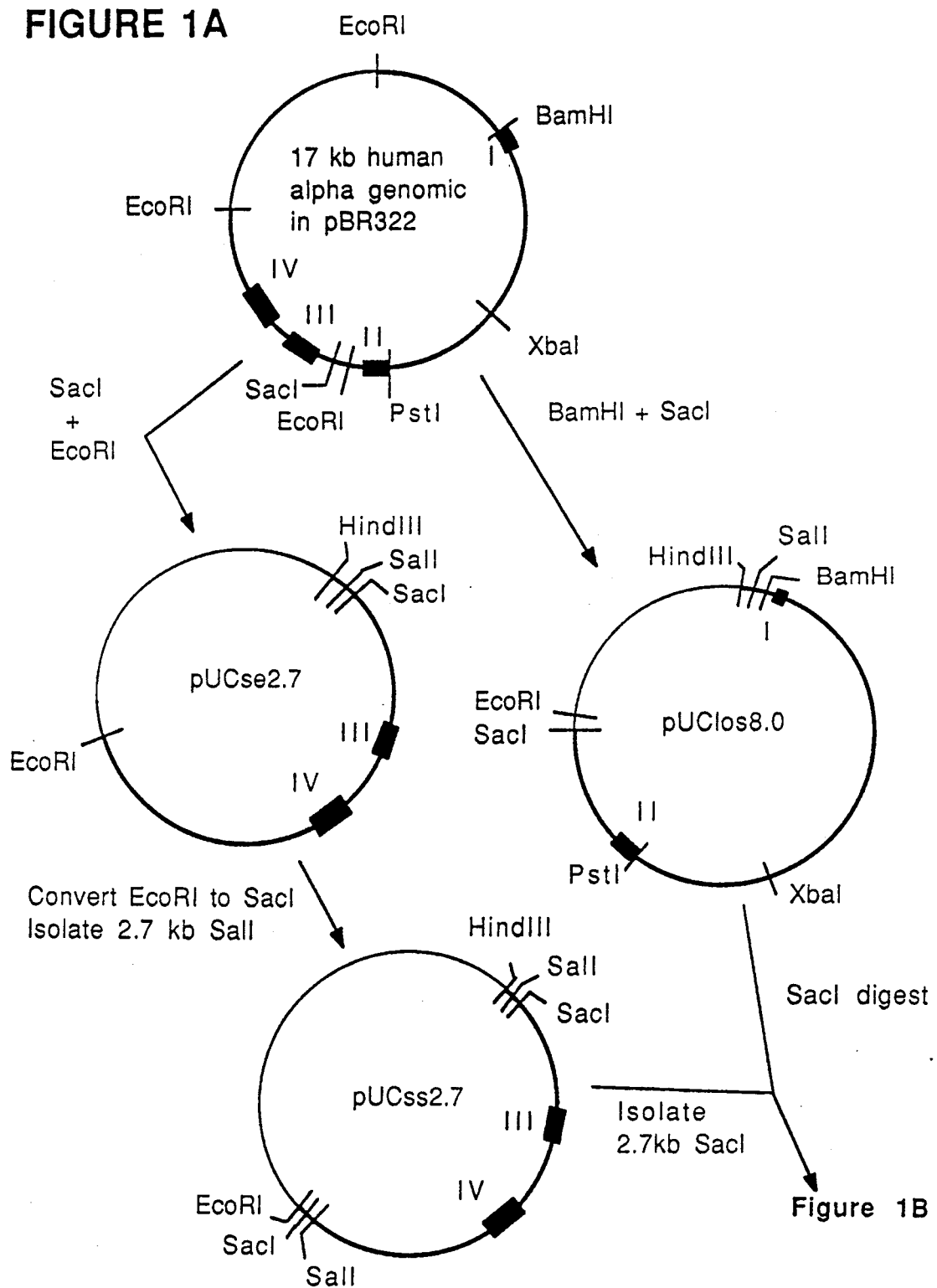
FIG. 1A and 1B: shows the strategy used to engineer the human $\alpha$ gene for expression in tissue culture cells. Important restriction endonuclease sites are indicated. Filled-in boxes represent $\alpha$ gene exons; heavy solid lines, $\alpha$ gene introns; thin solid lines, pBR322 or pUC18 vector; and zig-zag lines, pUC18 polylinker regions.
Figure 1B:
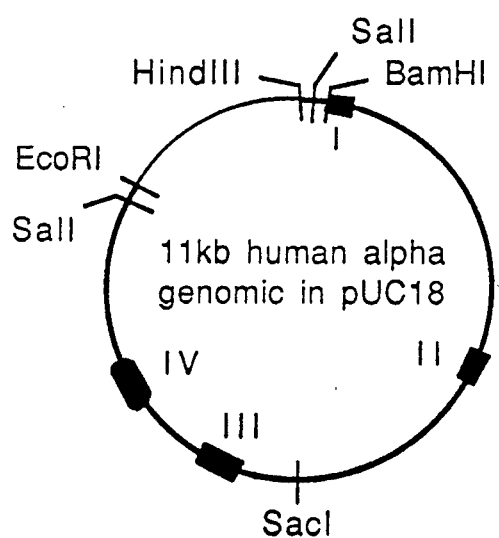

A. The complete human α subunit genomic clone can be conveniently obtained from a number of sources as a 17 kilobase pair (kb) EcoRI insert in pBR322. Because the α promoter has been shown to be tissue specific and would be unlikely to function efficiently in the tissue culture cells commonly used for heterologous gene expression, steps were taken to remove all 5' flanking sequences. The presence of internal EcoRI sites necessitated several subcloning steps prior to assembly of the trimmed genomic sequence. The engineering strategy advantageously used is diagrammed in FIG. 1. Two pUC18 subclones were constructed, the first with the 8.0 kb BamHI-SacI 5' piece (pUCbs8.0), and the second with the 3' 2.7 kb SacI-EcoRI piece (pUCse2.7). To generate a terminus compatible with the XhoI cloning sites in our expression vectors, pUCse2.7 was digested with EcoRI, the ends were blunted by treatment with the Klenow fragment of E. coli DNA polymerase I, and then SalI linkers were attached in a ligation reaction. Subsequent SalI restriction endonuclease digestion of the reaction mixture yielded a 2.7 kb human α SalI piece in addition to the 2.6 kb vector fragment. The 2.7 kb human α SalI piece was gel purified and re-inserted into into the SalI site of pUC18 (pUCss2.7). A clone was chosen which contained the SalI insert in the orientation which permitted isolation of the 2.7 kb α fragment as a SacI piece. This was gel purified and then inserted into the SacI site of pUCbs8.0 to assemble the complete coding sequence of the human α gene as an 11 kb insert in pUC18. The insert could be excised as a SalI fragment by virtue of a pre-existing SalI site in the pUC18 polylinker at the 5' end of the gene and the converted SalI site (from EcoRI) at the 3' end of the gene. The completed genomic α expression construction, henceforth referred to as the "full-length genomic α" sequence, included part of exon I (less the first 35 nucleotides which comprise the 5' untranslated region of the mRNA), all of exons II, III, and IV as well as the intervening sequences, and approximately two kilobase pairs (kb) of 3' flanking sequence. This was inserted into the XhoI site of the CLH3AXSV2DHFR expression vector (FIG. 2) so that transcription was directed by the mouse metallothionein-I (MT-I) promoter. The expression vector also contained the mouse dihydrofolate reductase (DHFR) gene for a selectable and amplifiable marker.

Figure 2:
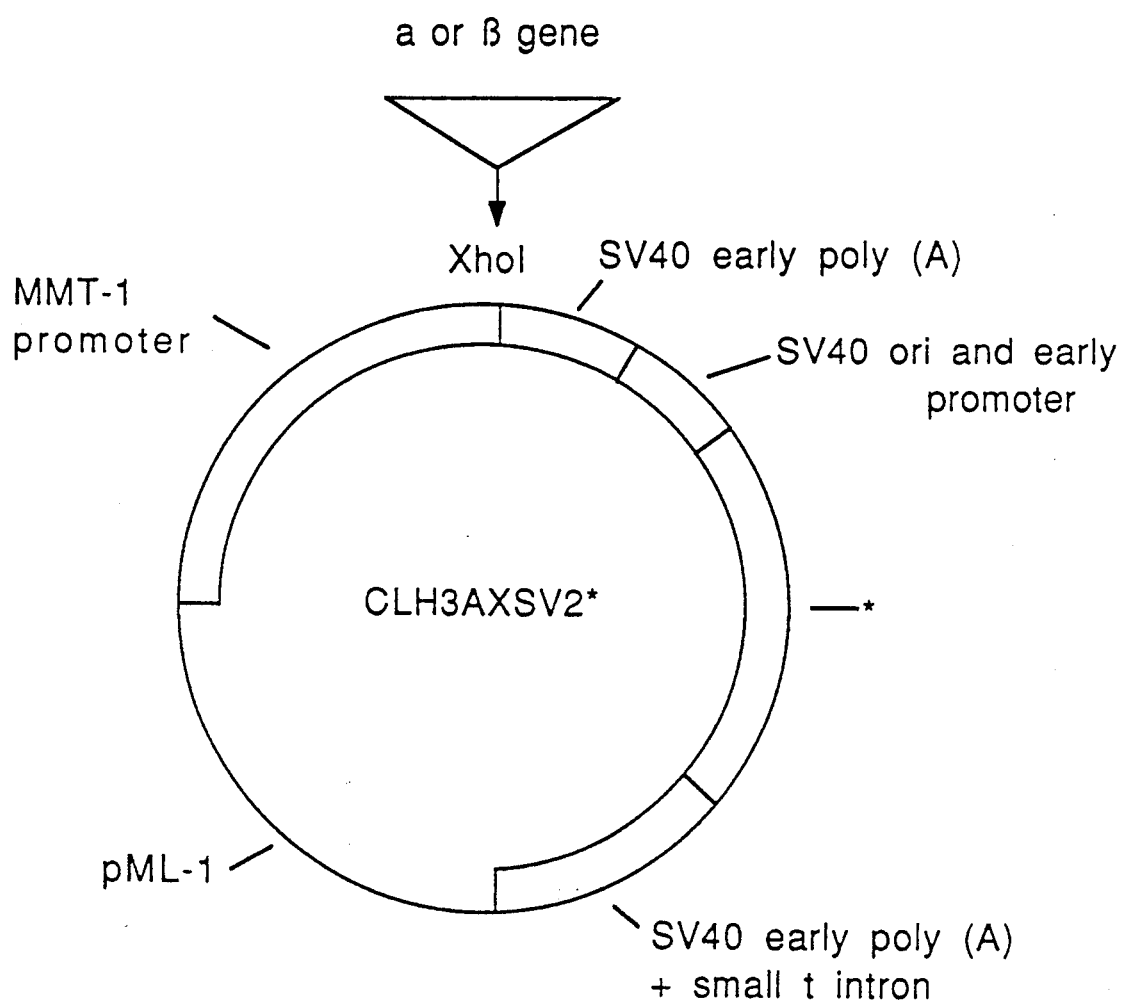
FIG. 2: shows the basic expression vector, CLH3AXSV2[DHFR, ODC, or TPA], used for stable or transient transfections. The position of the XhoI site used for insertion of $\alpha$ or $\beta$ subunit sequences is shown. Double solid lines represent sequences needed for mammalian cell expression. The relative positions of the promoter, polyadenylation, and marker gene regions are indicated. The single solid line represents the pBR322-derived pML-1 region necessary for propagation and selection (by ampicillin resistance) in E. coli.

B. The human α subunit cDNA was engineered for expression by digesting the full-length clone with NcoI, which spans the start ATG, and HindIII, which cleaves in the 3' untranslated region 215 base pairs (bp) downstream of the TAA stop codon. A 5' SalI site and Kozak consensus sequence (27) was provided by synthetic oligonucleotides, and a 3' SalI site by attaching linkers as described above. The DNA sequence of the engineered α subunit cDNA clone, which is approximately 600 bp in length, is shown in Table 7. This was inserted into the XhoI site of the CLH3AXSV2DHFR expression vector (FIG. 2). The endogenous 5' untranslated region and 3' polyadenylation signal were removed from the cDNA clone in the process of engineering and therefore were supplied by vector sequences: the MT-I promoter and the simian virus 40 (SV40) early polyadenylation signal, respectively.

C. The human FSHβ partial genomic clone used in this study was a 2.0 kb DdeI-Sau3A segment which contained the protein coding region of exon II in addition to 40 bp of sequence upstream of the start ATG, the protein coding region of exon III, and the 1.6 kb intron which separates the two exons (Table 7). The 5' DdeI and the 3' Sau3A sites had formerly been converted to EcoRI and BamHI sites, respectively, and therefore were not compatible with the current expression vectors. The partial FSHβ genomic clone was therefore supplied with SalI termini by blunting as described above and attaching commercially prepared SalI linkers. The SalI piece was then inserted into the XhoI site of CLH3AXSV20DC (FIG. 2), an expression vector structurally similar to CLH3AXSV2DHFR except that the DHFR coding region was replaced with that for murine ornithine decarboxylase (ODC).

Example 2

Comparison of the full-length genomic α cDNA α CLH3AXSV2DHFR transcription units in stable transfections The genomic α and cDNA α CLH3AXSV2DHFR constructions were compared by cotransfection of each α expression plasmid with the human FSHβ CLH3AXSV20DC expression plasmid and measurement of FSH dimer production.

A. Twenty-four hours before the transfections were to be done, 100 millimeter dishes were seeded with $7 \times 10^5$ DUKX CHO cells (DHFR-minus). Calcium phosphate precipitations were obtained by adding 31 microliters (μl) of 2 molar (M) CaCl$_2$ to the plasmid DNA suspended in 500 μl of transfection buffer [14 millimolar (mM) NaCl, 5 mM KCl, 0.7 mM Na$_2$HPO$_4$, 5.5 mM dextrose, and 20 mM HEPES (pH 7.5)]. Plasmid DNA amounts used were α (cDNA or genomic): 10 μg, and FSHβ: 30 μg. The precipitates were allowed to form for 45 minutes at room temperature. The culture medium was removed from the cells and replaced with the DNA precipitate. After allowing the cells to sit at room temperature for 20 minutes, 5 ml of culture medium was added to each dish and incubation was continued at 37° C. for 4 hours. The cells were then shocked for 3.5 minutes in 15% glycerol at 37° C. After incubation for 48 hours at 37° C. in culture medium the cells were split 1:10 and selection medium containing 0.02 methotrexate (MTX) was added. The selection medium used was α-minus modified Eagle's medium supplemented with 10% dialyzed fetal bovine serum and 1% L-glutamine. Ten to fourteen days later, foci were visible and were transferred to 24-well plates. Culture media from these were assayed for FSH dimer expression by using a specific monoclonal-based radioimmunoassay (Serono Diagnostics, Randolph, Mass.). Positive clones were transferred to T-25 flasks in selection medium which contained an increased MTX concentration of 0.1 μM. When the cultures reached confluence the media were again assayed for FSH dimer and the cells were counted to calculate the picogram per cell per 24 hour expression levels.

B. Human FSH dimer secretion levels measured in seven randomly selected clones from each of the human α genomic/FSHβ and human α cDNA/FSHβ cotransfections are presented in Table 1.

TABLE 1

| α GENOMIC-DHFR/FSHβ-ODC | | α cDNA-DHFR/FSHβ-ODC | |
|---|---|---|---|
| GFSH Cell Line | pg/cell/24h in 0.1 μM MTX | CFSH Cell Line | pg/cell/24h in 0.1 μM MTX |
| 1 | 0.43 | 18 | 0.003 |
| 3 | 1.95 | 37 | 0.03 |
| 4 | 0.50 | 51 | 0.08 |
| 5 | 0.70 | 57 | 0.02 |
| 7 | 1.44 | 60 | 0.056 |
| 8 | 1.18 | 66 | 0.051 |
| 9 | 2.56 | 70 | 0.013 |
| Avg. | 1.25 | Avg. | 0.04 |

The results show that FSH dimer expression is greatly enhanced in cells transfected with the full-length genomic α subunit sequence. The averaged expression levels indicate that the surprisingly large magnitude of the enhancement seen in this particular experiment was approximately thirty-fold.

C. To further demonstrate the superiority of the full-genomic α sequence, stable cell lines were transfected with the CLH3AXSV2DHFR expression vector that contained either the human α cDNA or the human α genomic clone. Expression rates of the free α subunit were compared. In all cases, the expression of human α subunit, as determined by a sensitive and specific radioimmunoassay, was never greater than 0.05 pg/cell/24h for the cDNA-containing cell lines. As detailed in Table 2, cells that were transfected with the genomic α clone expressed 5-20 times greater levels of the protein:

TABLE 2

| Alpha Cell Line | Expression Level pg/cell/24h |
|---|---|
| 2 | 0.32 |
| 10 | 0.36 |
| 12 | 0.57 |
| 17 | 0.37 |
| 18 | 0.39 |
| 38 | 1.28 |
| 47 | 0.63 |
| 51 | 0.26 |

Example 3

Thyroid stimulating hormone constructions

To demonstrate the effectiveness and broad application of this invention, stably transfected CHO cell lines were prepared by cotransfection of the full-length human genomic α sequence in CLH3AXSV2DHFR with a partial genomic TSHβ sequence in CLH3AX-SV2ODC. The partial genomic TSBβ fragment used in this experiment consisted of the protein coding regions of exon II and III, and the 0.5 kb intron which separated the two exons (Table 9). All 5' and 3' regions flanking the protein coding sequence of TSHβ were removed in this particular construction. Following cotransfection with the two expression vectors, stable cell lines were cultured and analyzed for their ability to express TSH. Expression levels of the dimer, as determined by a sensitive and specific radioimmunoassay, are listed in Table 3. Previous studies with the transfection of the cDNA for the α subunit with the genomic TSHβ clone had demonstrated that expression levels were usually below the sensitivity of the radioimmunoassay, usually less than 0.02 pg/cell/24 h.

TABLE 3

| TSH Cell Line | Expression Rate pg/cell/24h |
|---|---|
| 7 | 0.19 |
| 8 | 0.22 |
| 10 | 0.24 |
| 12 | 0.24 |
| 37 | 0.13 |
| 48 | 2.97 |

TSH production, then, like FSH production, can be greatly enhanced by use of the full genomic α sequence, rather than the α cDNA sequence, in mammalian cell transfections. In this experiment the range of TSH production enhancement was 6 to 100 fold.

Example 4

Introns and expression enhancement

The human α genomic construction differed from the human α cDNA construction not only in that it contained introns, but also in that it contained endongenous 5' untranslated sequence, the endogenous polyadenylation signal, and additional 3' flanking sequences. Therefore, one could not infer from the results of the previous set experiments which genomic regions contributed to the enhanced expression.

A. To determine if the introns within the genomic α sequence were responsible for the elevated α subunit levels, we inserted a 2 kb XbaI-PstI portion of the human α intron A between the mouse MT-I 5' untranslated region and the α cDNA sequence in the CLH3AXSV2TPA vector (FIG. 2). The truncated intron retained the endogenous splice acceptor, but the splice donor was supplied by a synthetic oligonucleotide.

B. Another plasmid was constructed to test the effect of a heterologous intron on α subunit expression. In this construction, a 130 bp intron from the MOPC41 immunoglobulin κ gene (5) was inserted between the mouse MT-I 5' untranslated region and the α cDNA sequence. No transcriptional enhancer elements were included in this particular intervening sequence.

C. The intron-containing α cDNA constructs were compared to the original α cDNA construct and the full length genomic α sequence by transient transfection of COS-7 cells with the plasmid DNA and analysis of mRNA levels by northern blotting. In this experiment, the tissue plasminogen activator (tPA) cDNA served as an internal standard and was used to correct for the variations in the transfection efficiency of different plasmid constructions and thus normalize measured α subunit mRNA levels. Transfections were done in duplicate using the DEAE-dextran protocol of Seed and Aruffo (28). Two days after transfection, total cellular RNA was isolated from the cells. The RNA (5 micrograms) was fractionated on formaldehyde gels and then transferred to nylon membranes using standard northern blotting techniques. The membranes were then hybridized to either a $^{32}$P-labeled human α or a $^{32}$P-labeled tPA probe and the resulting signals were quantitated on a Betascope Model 603 blot analyzer (Betagen Corp., Waltham, Mass.). Normalized α mRNA values for relative comparisons were calculated by dividing the number of α counts by the number of tPA counts and then averaging the numbers obtained for duplicate samples. Results of the experiment are shown in Table 4.

TABLE 4

| Plasmid Construction | | Betascope counts α probe | tPA probe | Normalized Values (α/tPA) | Average of Duplicates |
|---|---|---|---|---|---|
| 1. α genomic | A | 6315 | 958 | 6.6 | 7 |
| | B | 7836 | 1177 | 6.7 | |
| 2. α cDNA + α IVS | A | 25353 | 1294 | 19.6 | 21 |
| | B | 34616 | 1559 | 22.2 | |
| 3. α cDNA + Ig IVS | A | 31743 | 1690 | 18.8 | 17 |
| | B | 37495 | 2327 | 16.1 | |
| 4. α cDNA | A | 3891 | 2608 | 1.5 | 1 |
| | B | 3671 | 3341 | 1.1 | |

The results indicated that the cDNA constructions which contained either the human α intron (No. 2) or the immunoglobulin intron (No. 3) were more efficient as the full length genomic sequence (No. 1) in the accumulation of α subunit mRNA. Specifically, the normalized α subunit mRNA levels were 7- to 21-fold higher than those produced by the cDNA construct (No. 4) without an intron. We have therefore unexpectedly discovered that introns, and not the 5' or 3' regions which flank the α subunit protein coding sequence, are primarily responsible for the increased expression levels and that the effect is due, at least in part, to an increased accumulation of α subunit mRNA.

Example 5

Expression enhancement not due to increased transcription rates

Nuclear runoff transcription assays were used to determine if the high level of genomic α-induced mRNA accumulation was due to an increased transcription rate. Transient transfection of COS-7 cells with the α genomic and α cDNA-containing CLH3AXSV2TPA plasmids was done as described in Example 4. Standard methods were used in the preparation of nuclei and for the runoff transcription assay (Current Protocols in Molecular Biology; Ausubel, F.M. et al., ed.; John Wiley & Sons, New York, N.Y.). The DNA probes for α, DHFR, and tPA were gel purified insert sequences and approximately 0.25 μg of each were slot blotted in duplicate onto nitrocellulose membranes. The membranes were hybridized to [$^{32}$P-UTP] labeled nuclear runoff RNA prepared from COS-7 cells that had been transfected with no DNA (mock), the full-length human α genomic clone in CLH3AXSV2TPA, or the human α cDNA clone in CLH3AXSV2TPA. The hybridization signal was quantitated on a Betascope Model 603 blot analyzer (Betagen, Corp., Waltham, Mass.). Normalized values for the transcription rate were obtained by dividing the averaged α counts by the averaged tPA counts. The monkey DHFR nuclear runoff RNA should not hybridize to the mouse DHFR DNA probe sequence in the conditions used for this experiment, and therefore serves as a negative control. The relative transcription rate results are summarized in Table 5, below.

TABLE 5

| | Nuclear runoff RNA | | | | | |
|---|---|---|---|---|---|---|
| | Mock COS-7 | | α cDNASV2TPA | | αgenomic/ SV2TPA | |
| DNA Probes | 1 | 2 | 1 | 2 | 1 | 2 |
| α cDNA | 119 | 160 | 2093 | 2155 | 492 | 620 |
| tPA | 387 | 413 | 18022 | 17667 | 8486 | 7388 |
| DHFR | 230 | 307 | 54 | 0 | 32 | 765* |
| Rate Ratios: α/tPA | — | | 0.12 | | 0.07 | |

*Non-specific background rendered this value artificially high

In this particular experiment the runoff transcription rate of the α cDNA (0.12) was surprisingly higher than that of the genomic α sequence (0.07). An increased transcription rate is therefore not the mechanism by which the genomic α sequence generates higher α subunit expression levels.

Example 6

TSHβ Subunit expression is intron-dependent

Figure 3A:
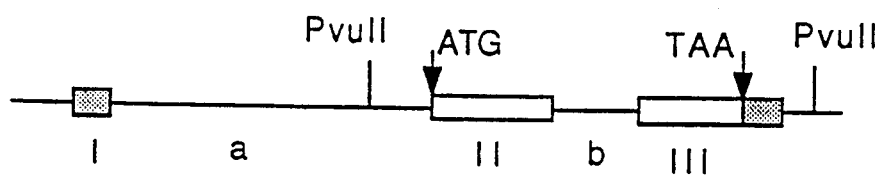
FIG. 3: part A shows the full-length TSH$\beta$ gene. The positions of the three exons (I, II, and III), two introns (a, b), start ATG, and stop codon (TAA) are indicated. The PvuII sites used to isolate the fragment from which the partial constructions were derived are also indicated. Hatched boxes denote noncoding exon sequences. Part B shows the partial genomic constructions used to compare TSHβ mRNA accumulation in transiently transfected COS-7 cells. TSHβ0.9 consists of the two coding exons separated by the endogenous IVS with all sequences upstream of the start ATG and downstream of the TAA removed (sequence shown in Table 9). TSHβ1.2 and TSHβ2.0 contain, in addition, about 300 base pairs of intron A and were constructed by adding a synthetic splice donor (Δ) to allow splicing of the truncated intron. TSHβ2.0 retained the endogenous polyadenylation signal (Δ) and about 0.8 kb of additional 3 flanking sequence.
Figure 3B:
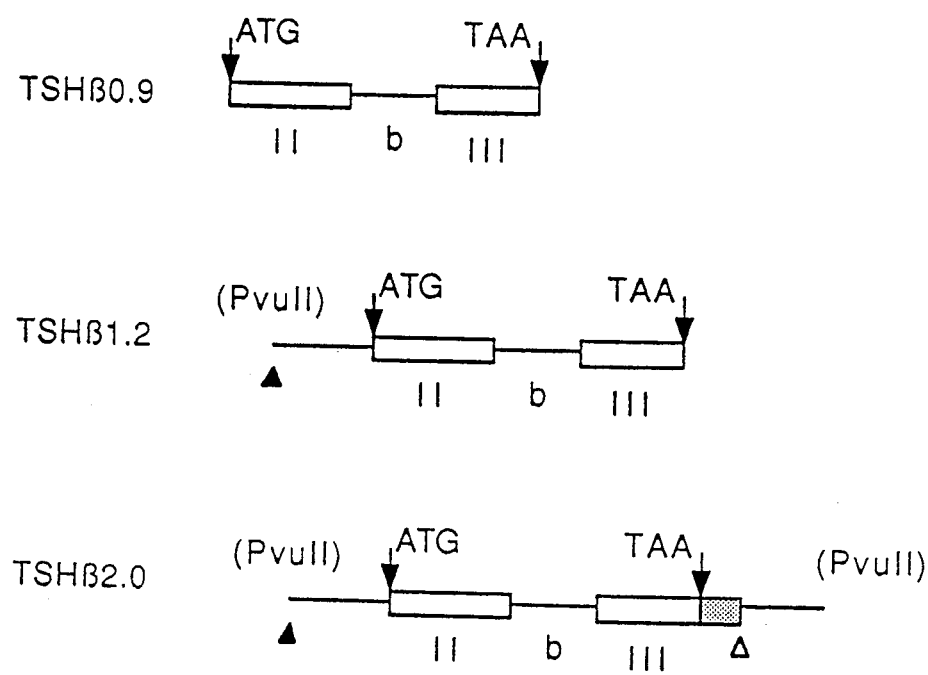
Figure 4:
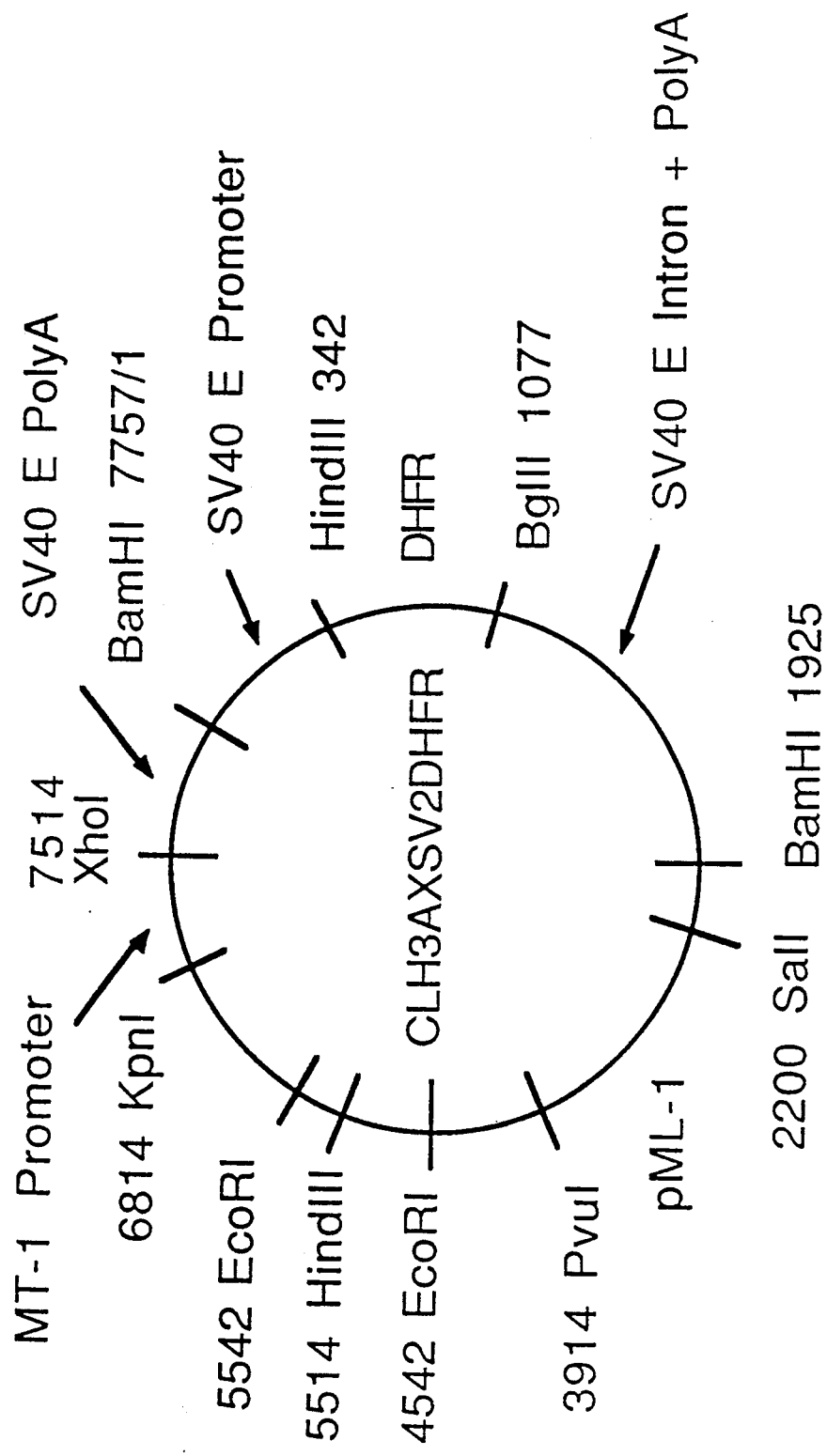
FIG. 4: describes CLH3AXSV2DHFR. This vector was constructed from the following components: (i) the dihydrofolate reductase (DHFR) transcriptional unit (nucleotide numbers 1to 1925 of FIG. 4) which consists of the SV40 early region promoter (33, 34), the mouse DHFR gene (REFS) and the SV40 small T intron and early region polyadenylation signal sequences (33, 34); (ii) the bacterial plasmid vector sequences of pML (nucleotide numbers 2201 to 4542 of FIG. 4) derived from the pBR322 vector (29) from which a 1370 base pair sequence has been deleted (32); and (iii) the metallothionein promoter (nucleotide numbers 4542 to 7514 of FIG. 4) derived from the mouse metallothionein-1 gene (30, 31) from which the introns and polyadenylation signal sequences have been removed; and (iv) the SV40 early region polyadenylation signal sequences (nucleotide numbers 7514 to 7751 of FIG. 4) (33, 34). The tPA analogues were inserted into the vector as a SalI fragment at the unique XhoI site. The orientation of the insert relative to the promoter and polyadenylation sequences was determined by restriction enzyme analysis.

A. The full-length genomic TSHβ gene (14a) is diagrammed in FIG. 3, Part A. The positions of the three exons (I, II, and III), two introns (a, b), start ATG, and stop codon (TAA) are indicated. The PvuII sites were separated by approximately 2 kb of DNA sequence which included exons II and III and contained the complete protein coding sequence for TSHβ. The TSHβ partial genomic constructions used in this study were derived from the 2 kb PvuII fragment and are diagrammed in Table 3B. TSHβ 0.9 (0.9 kb) was the same construct used in stable transfections in Example 1 and consisted of the two coding exons separated by the endogenous intervening sequence with all sequences upstream of the start ATG and downstream of the TAA removed. TSHβ 1.2 (1.2 kb) and TSHβ 2.0 (2.0 kb) contained, in addition, about 300 base pairs of intron A and were constructed by adding a synthetic splice donor to allow splicing of the truncated intron. TSHβ 2.0 retained the endogenous polyadenylation signal and about 0.8 kb of additional 3' flanking sequence.

B. Duplicate cultures (A, B) of COS-7 cells were transfected, using the protocol described in Example 4, with CLH3AXSV2DHFR plasmids which contained one of the following partial genomic fragments: (1) TSHβ 0.9, (2) TSHβ 1.2, or (3) TSHβ 2.0. The genes were inserted into the XhoI cloning site so that transcription would be initiated by the MT-I promoter and, in the case of TSHβ 0.9 and TSHβ 1.2, terminated by the SV40 early polyadenylation signal. After 48 hours of incubation, total cellular RNA was isolated from the cells. The RNA (9 micrograms) was fractionated on formaldehyde gels and then transferred to nylon membranes using standard northern blotting techniques. The membranes were hybridized to either a $^{32}$P-labeled mouse MT-I probe (to detect the TSHβ mRNA which also contains about 50 base pairs MT-I 5' untranslated sequence) or a $^{32}$P-labeled DHFR probe (to compare transfection efficiencies). The resulting signals were quantitated on a Betascope Model 603 blot analyzer (Betagen Corp., Waltham, Mass.). Normalized TSHβ mRNA values for relative comparisons were calculated by dividing MT-I counts by DHFR counts. Normalized values obtained for duplicate transfections were then averaged and divided by the number obtained for TSHβ 0.9. The comparative results obtained for accumulation of mRNA are summarized in Table 6.

TABLE 6

| Plasmid Construction | | Betascope Counts MT Probe | Betascope Counts DHFR Probe | Normalized Values (MT/DHFR) | Relative Values (averaged) |
|---|---|---|---|---|---|
| 1. TSHβ 0.9 | A | 983 | 3985 | 0.25 | 1 |
|  | B | 834 | 4118 | 0.20 |  |
| 2. TSHβ 1.2 | A | 4480 | 254 | 17.6 | 60 |
|  | B | 2748 | 285 | 9.6 |  |
| 3. TSHβ 2.0 | A | 1381 | 1209 | 1.2 | 5 |
|  | B | 1632 | 1254 | 1.3 |  |

C. The results indicated that the two constructs which retained a portion of the first intron (TSHβ 1.2 and TSHβ 2.0) yielded 5-60 fold higher mRNA accumulation than did the construct which contained no sequences from the first intron. Therefore TSHβ gene expression, like α subunit gene expression, is intron-dependent. Of interest was the unexpected observation that intron B, which was present in all the constructs and was in the protein coding region, did not confer optimal enhancement. This suggested either that there are specific sequences in the first intron of the TSHβ gene which increased mRNA accumulation or, more likely, that the position of the intron (close to the 5' end of the mRNA) was the crucial factor. That intron-dependent gene expression may be affected by the placement of the intron in the transcription unit is supported by preliminary experiments with the human α cDNA. Insertion of the κ immunoglobulin gene intron in the 3' untranslated region of the mRNA, between the α cDNA and the SV40 polyadenylation region, resulted in no increased mRNA accumulation when compared to the unaltered α cDNA.

D. Since TSHβ 1.2 yielded 10-fold higher amounts of mRNA than TSHβ 2.0, it is probable that the endogenous polyadenylation signal and 3' flanking sequence carried on TSHβ 2.0 are not required for efficient mRNA formation, and may actually be detrimental. Alternatively, the disparity in mRNA accumulation between TSHβ 1.2 and TSHβ 2.0 may be related to the different distances between the MT-I promoter and the SV40 early promoter (driving the DHFR) in the two plasmid constructions. The closer proximity (0.8 kb) of the two promoters in the TSHβ 1.2 construction may permit increased interaction between the SV40 enhancer elements and the MT-I promoter, thereby increasing the rate of transcription from the latter.

Because of the similarity of α and TSHβ gene structure among various mammals, we expect that our findings based on the human α and TSHβ subunits apply equally to those of other species, such as the bovine, equine, porcine, baboon and monkey. Likewise, LHβ and FSHβ subunit genes may show a similar dependence on genomic DNA structure for optimal expression and these requirements should apply across species.

Construction of expression vectors will be advantageously simplified by application of the knowledge that certain genomic regions, such as introns, are important for mRNA accumulation, and that the position of these regions in the transcription unit may be important. For example, these genomic regions may be subcloned or synthesized and included in constructions with the α and β subunit cDNA sequences. The cDNA clones are often easier to obtain and to engineer than the much larger genomic clones. Thus, this discovery will simplify the development of cell lines which produce high levels of hormone and, ultimately, will permit large scale production of these proteins at a lower cost. These and other aspects and variations of the present invention will now be readily apparent to those skilled in the art and are not deemed to depart from either the spirit or the scope of the present invention.

References

1. Hamer, D. H. and Leder, P. (1979) Cell 17, 737-747
2. Hamer, D. H. and Leder, P. (1979) Cell 18, 1299-1302
3. Banerji, J. et al. (1983) Cell 33, 729-740
4. Gillies, S. D. et al. (1983) Cell 33, 717-728
5. Queen, C. and Baltimore, D. (1983) Cell 33, 741-748
6. Gross, M. K. et al. (1987) Mol. Cell. Biol. 7, 4576-4581
7. Kaetzel, D. M. and Nilson, J. H. (1988) J. Biol. Chem. 263, 6344-6351
8. Fiddes, J. C. and Goodman, H. M. (1981) J. Mol. Appl. Genetics 1, 3-18
9. Goodwin, R. G. et al. (1983) Nucl. Acids Res. 11, 6873-6882
10. Virgin, J. et al. (1985) J. Biol. Chem. 260, 7072-7077
11. Talmadge, K. et al. (1984) Nature 307, 37-40
12. Kim, K. E. et al. (1988) DNA 7, 227-233
13. Watkins, P. C. et al. (1987) DNA 6, 205-212
14. Wondisford, F. E. et al. (1988) Mol. Endo. 2, 32-39
14a. Wondisford, F. E. et al. (1988) J. Biol. Chem. 263, 12538-12542
15. Ramabhadran, T. V. et al. (1984) Proc. Natl. Acad. Sci. USA 81, 6701-6705
16. Reddy, V. B. et al. (1985) Proc. Natl. Acad. Sci. USA 82, 3644-3648

17. Watanabe, S. et al. (1987) Biochem. Biophys. Res. Comm. 149, 1149-1155
18. Matzuk, M. M. et al. (1987) Proc. Natl. Acad. Sci. USA 84, 6354-6358
18a. Matzuk, M. and Boime, I. (1988) J. Cell Biol. 106, 1049-1059
19. Kaetzel, D. M. et al. (1985) Proc. Natl. Acad. Sci. USA 82, 7280-7283
20. Buchman, A. R. and Berg, P. (1988) Mol. Cell. Biol. 8, 4395-4405
21. Lee, F. et al. (1981) Nature 294, 228-232
22. Evans, M. J. and Scarpulla, R. C. (1988) Mol. Cell. Biol. 8, 35-41
23. Rossouw, C. M. S. et al. (1987) J. Biol. Chem. 262, 15151-15157
24. Brinster, R. L. et al. (1987) Proc. Natl. Acad. Sci. USA 85, 836-840
25. Pfarr, D. S. et al. (1986) DNA 5, 115-122
26. Ross, J. and Kobs, G. (1986) J. Mol. Biol. 188, 579-593
27. Kozak, M. (1984) Nucl. Acids Res. 12, 857-872
28. Seed, B. and Aruffo, A. (1987) Proc. Natl. Acad. Sci. USA 84, 3365
29. Bolivar, F., Rodriguez, R. L., Green, P. J., Betlach, M. C., Heynecker, H. L., Boyer, H. W., Crosa, G. F. and Falkow, S. (1977) Gene 2:95.
30. Glanville, N., Durnham, D. M. and Palmiter, R. D. (1981) Nature 292:267-269.
31. Hamer, D. H. and Walling, M. (1982) J. Mol. Appl. Gen. 1:273-288.
32. Lusky, M. and Botchan, M. (1981) Nature 293:79-81.
33. Reddy, V. B., Thimmapaya, B., Dhar, R., Subramanian, K. N., Zain, B. S., Pan, J., Ghosh P. K., Celma, M. L. and Weissman, S. M. (1978) Science 200:494.
34. Tooze, J. (ed.), DNA Tumor Viruses; Molecular Biology of Tumor Viruses; 2nd Ed., Cold Spring Harbor Laboratory, New York 1981.
35. Chiang T.-R. and McConlogue, L. (1988), Mol. Cell. Biol. 8:764-769.

Except as otherwise stated, procedures and techniques used are generally as reported and conventional in the art such as is described by Maniatis et al, A Cloning Manual, Cold Spring Harbor (1982). All references cited above or in the specification are fully incorporated herein by reference.

TABLE 7

```
      Sal 1      Kozak
                        Met Asp Tyr Tyr Arg Lys Tyr Ala Ala Ile Phe Leu Val Thr Leu
  1  GTCGACGCCGCCACCATGGATTACTACAGAAAATATGCAGCTATCTTTCTGGTCACATTG      60

Ser Val Phe Leu His Val Leu His Ser Ala Pro Asp Val Gln Asp Cys Pro Glu Cys Thr
 61  TCGGTGTTTCTGCATGTTCTCCATTCCGCTCCTGATGTGCAGGATTGCCCAGAATGCACG    120

Leu Gln Glu Asn Pro Phe Phe Ser Gln Pro Gly Ala Pro Ile Leu Gln Cys Met Gly Cys
121  CTACAGGAAAACCCATTCTTCTCCCAGCCGGGTGCCCCAATACTTCAGTGCATGGGCTGC    180

Cys Phe Ser Arg Ala Tyr Pro Thr Pro Leu Arg Ser Lys Lys Thr Met Leu Val Gln Lys
181  TGCTTCTCTAGAGCATATCCCACTCCACTAAGGTCCAAGAAGACGATGTTGGTCCAAAAG    240

Asn Val Thr Ser Glu Ser Thr Cys Cys Val Ala Lys Ser Tyr Asn Arg Val Thr Val Met
241  AACGTCACCTCAGAGTCCACTTGCTGTGTAGCTAAATCATATAACAGGGTCACAGTAATG    300

Gly Gly Phe Lys Val Glu Asn His Thr Ala Cys His Cys Ser Thr Cys Tyr Tyr His Lys
301  GGGGGTTTCAAAGTGGAGAACCACACGGCGTGCCACTGCAGTACTTGTTATTATCACAAA    360

Ser
361  TCTTAAATGTTTTACCAAGTGCTGTCTTGATGACTGCTGATTTTCTGGAATGGAAAATTA    420

421  AGTTGTTTAGTGTTTATGGCTTTGTGAGATAAAACTCTCCTTTTCCTTACCATACCACTT    480

481  TGACACGCTTCAAGGATATACTGCAGCTTTACTGCCTTCCTCCTTATCCTACAGTACAAT    540

541  CAGCAGTCTAGTTCTTTTCATTTGGAATGAATACAGCATTAAGCTGGTCGAC      592
                                                             Sal 1
```

The engineered alpha subunit cDNA sequence. Restriction endonuclease sites and Kozak consensus region which were supplied by synthetic oligonucleotides are indicated. The alpha subunit amino acid sequence is also shown.

TABLE 8

```
    Sal 1
                                                         Met Lys Thr Leu Gln Phe P
  1  TCAGTTTCTAGTGGGCTTCATTGTTTGCTTCCCAGACCAGGATGAAGACACTCCAGTTTT      60 he Phe Leu Phe Cys Cys Trp Lys Ala Ile Cys Cys Asn Ser Cys Glu Leu Thr Asn Ile T
 61  TCTTCCTTTTCTGTTGCTGGAAAGCAATCTGCTGCAATAGCTGTGAGCTGACCAACATCA    120 hr Ile Ala Ile Glu Lys Glu Glu Cys Arg Phe Cys Ile Ser Ile Asn Thr Thr Trp Cys A
121  CCATTGCAATAGAGAAAGAAGAATGTCGTTTCTGCATAAGCATCAACACCACTTGGTGTG    180 la Gly Tyr Cys Tyr Thr Arg            1.6 kb IVS
181  CTGGCTACTGCTACACCAGGGTAGGTACC............TAGAGCAAGCAGTATTCA    1674

1675 ATTTCTGTCTCATTTTGACTAAGCTAAATAGGAACTTCCACAATACCATAACCTAACTCT    1734
```

TABLE 8-continued

```
                 Asp Leu Val Tyr Lys Asp Pro Ala Arg Pro Lys Ile Gln Lys T
1735  CTTCTTAAACTCCTCAGGATCTGGTGTATAAGGACCCAGCCAGGCCCAAAATCCAGAAAA       1794 hr Cys Thr Phe Lys Glu Leu Val Tyr Glu Thr Val Arg Val Pro Gly Cys Ala His His A
1795  CATGTACCTTCAAGGAACTGGTATATGAAACAGTGAGAGTGCCCGGCTGTGCTCACCATG       1854 la Asp Ser Leu Tyr Thr Tyr Pro Val Ala Thr Gln Cys His Cys Gly Lys Cys Asp Ser A
1855  CAGATTCCTTGTATACATACCCAGTGGCCACCCAGTGTCACTGTGGCAAGTGTGACAGCG       1914 sp Ser Thr Asp Cys Thr Val Arg Gly Leu Gly Pro Ser Tyr Cys Ser Phe Gly Glu Met L
1915  ACAGCACTGATTGTACTGTGCGAGGCCTGGGGCCCAGCTACTGCTCCTTTGGTGAAATGA       1974 ys Glu
1975  AAGAATAAAGATCcggatcggtcgac    2000
                    └─┬─┘
                     Sal 1
```

The engineered human FSH beta subunit partial genomic sequence. Positions of the terminal SalI sites are indicated. Nucleotides in lower case at the 3' terminus results from attachment of synthetic linkers. The FSH beta amino acid sequence marks the coding regions of exons II and III. The dotted line represents uncharacterized intervening sequence (IVS).

TABLE 9

```
        Sal 1      Kozak
         ⌢          ⌢       Met Thr Ala Leu Phe Leu Met Ser Met Leu Phe Gly Leu Ala Cys
  1  GTCGACGCCGCCACCATGACTGCTCTCTTTCTGATGTCCATGCTTTTTGGCCTTGCATGT        60

Gly Gln Ala Met Ser Phe Cys Ile Pro Thr Glu Tyr Thr Met His Ile Glu Arg Arg Glu
 61  GGGCAAGCGATGTCTTTTTGTATTCCAACTGAGTATACAATGCACATCGAAAGGAGAGAG       120

Cys Ala Tyr Cys Leu Thr Ile Asn Thr Thr Ile Cys Ala Gly Tyr Cys Met Thr Arg
121  TGTGCTTATTGCCTAACCATCAACACCACCATCTGTGCTGGATATTGTATGACACGGGTA       180

181  TGTAGTTCATGTCACTTCTTTTGGCTGTAAATTATATAAGCCCTGAAGAAGTCCATTCCT       240

241  ATATAGAAAGGAAATGAAATAAATCACAACCTCATTTCCCAAATCTAATGGTTATTGGCT       300

301  CCTTAGAAGCAGAGTACACAGGTTACAATATTATGTGAATCTACTCAGCACAATGGATAC       360

361  GCATAATTTTATAACAGTTTTGTGTCCCAGCTTTACTTAAACCTTATCTTGTTCCCATGA       420

421  TCAACGATGAAAGAGAGGAGGGTCTCACTTTTGTCTCTGTAGAATTCAACGTGGTTAAGT       480

481  TGGTATTGGAGAATGGGGCTAAGCAATTCTTTCCCAGTTGTATTTGTGATGAAGGAATAT       540

541  AAGTGAATTTATTTTTATGTTTCTATTATCTATATGTTTCCTAAAGTCCTGTCACATTAT       600

Asp Ile Asn Gly Lys Leu Phe Leu Pro Lys Tyr Al
601  GCTCTCTTTTCTGTTCTTTCCCCAGGATATCAATGGCAAACTGTTTCTTCCCAAATATGC       660 a Leu Ser Gln Asp Val Cys Thr Tyr Arg Asp Phe Ile Tyr Arg Thr Val Glu Ile Pro Gl
661  TCTGTCCCAGGATGTTTGCACATATAGAGACTTCATCTACAGGACTGTAGAAATACCAGG       720 y Cys Pro Leu His Val Ala Pro Tyr Phe Ser Tyr Pro Val Ala Leu Ser Cys Lys Cys Gl
721  ATGCCCACTCCATGTTGCTCCCTATTTTTCCTATCCTGTTGCTTTAAGCTGTAAGTGTGG       780 y Lys Cys Asn Thr Asp Tyr Ser Asp Cys Ile His Glu Ala Ile Lys Thr Asn Tyr Cys Th
781  CAAGTGCAATACTGACTATAGTGACTGCATACATGAAGCCATCAAGACAAACTACTGTAC       840 r Lys Pro Gln Lys Ser Tyr Leu Val Gly Phe Ser Val End
841  CAAACCTCAGAAGTCTTATCTGGTAGGATTTTCTGTCTAAGTCGAC          886
                                                  ⌣
                                                 Sal 1
```

The engineered TSH beta subunit partial genomic sequence. SalI sites and Kozak consensus sequence supplied by synthetic oligonucleotides are indicated. The TSH beta amino acid sequence marks the coding regions of exons II and III.

What is claimed is:

1. A method for the production of thyroid stimulating hormone comprising the steps of:

a) providing a first vector comprising a promoter, a DNA fragment encoding for the alpha subunit of said thyroid stimulating hormone and comprising at least one intron, and a terminating sequence, and a second vector comprising a promoter, a DNA fragment TSHB 1.2 or TSHB 2.0 encoding for the beta subunit of said thyroid stimulating hormone consisting essentially of coding exons II and III separated by an endogenous intervening sequence, and one intron about 300 base pairs in length positioned upstream of and adjacent to exon II, and a terminating sequence;

b) transforming host cells with said vectors; and c) culturing said transformed cells under conditions whereby said thyroid stimulating hormone is produced.

2. The method of claim 1 wherein said DNA fragment encoding said α subunit further comprises a plurality of introns, 3' and 5' flanking regions, endogenous 5' untranslated sequence and polyadenylation signal.

3. The method of claim 1 wherein said selected dimeric protein is human thyroid stimulating hormone.

4. The method of claim 1 wherein said selected dimeric protein is non-human thyroid stimulating hormone.

5. The method of claim 3 wherein the DNA fragment for the beta subunit of human thyroid stimulating hormone is a 1.2 kb DNA fragment containing the two coding exons separated by an endogenous intervening sequence, but without the endogenous polyadenylation signal or additional 3' flanking sequence.

6. The method of claim 3 wherein the DNA fragment for the beta subunit of human thyroid stimulating hormone is a 2.0 kb DNA fragment containing the two coding exons separated by an endogenous intervening sequence, and including the endogenous polyadenylation signal and 0.8 kb of additional 3' flanking sequence.

* * * * *